(12) United States Patent
Elghazzawi et al.

(10) Patent No.: US 8,160,698 B2
(45) Date of Patent: Apr. 17, 2012

(54) CPR SENSITIVE ECG ANALYSIS IN AN AUTOMATIC EXTERNAL DEFIBRILLATOR

(75) Inventors: Ziad E. Elghazzawi, Newton, MA (US); Edward Neil Akiyama, Bedford, MA (US); Ciro A. Dela Vega, Newburyport, MA (US); Donald R. Boucher, Andover, MA (US)

(73) Assignee: ZOLL Medical Corporation, Chelsmford, MA (US)

( * ) Notice: Subject to any disclaimer, the term of this patent is extended or adjusted under 35 U.S.C. 154(b) by 709 days.

(21) Appl. No.: 11/264,819

(22) Filed: Nov. 1, 2005

(65) Prior Publication Data
US 2006/0122648 A1    Jun. 8, 2006

Related U.S. Application Data

(63) Continuation of application No. 10/370,036, filed on Feb. 19, 2003, now Pat. No. 6,961,612.

(51) Int. Cl.
*A61N 1/00* (2006.01)
*A61H 31/00* (2006.01)

(52) U.S. Cl. .................... 607/5; 607/4; 607/6; 601/41
(58) Field of Classification Search ................ 607/5, 4, 607/6; 601/41
See application file for complete search history.

(56) References Cited

U.S. PATENT DOCUMENTS

| | | | |
|---|---|---|---|
| 3,865,101 A | 2/1975 | Saper et al. | |
| 4,059,099 A | 11/1977 | Davis | |
| 4,088,138 A | 5/1978 | Diack et al. | |
| RE30,372 E | 8/1980 | Mirowski et al. | |
| 4,296,755 A | 10/1981 | Judell | |
| 4,355,634 A | 10/1982 | Kanter | |
| 4,588,383 A * | 5/1986 | Parker et al. ................ | 434/265 |
| 4,610,254 A * | 9/1986 | Morgan et al. ................ | 607/6 |

(Continued)

FOREIGN PATENT DOCUMENTS

EP    1057451    12/2000

(Continued)

OTHER PUBLICATIONS

Aase et al., "CPR Artifact Removal from Human ECG Using Optimal Multichannel Filtering", IEEE Transactions on Biomedical Engineering, vol. 47:11, pp. 1440-1449 (2000).

(Continued)

*Primary Examiner* — Niketa I Patel
*Assistant Examiner* — Nicole F Lavert
(74) *Attorney, Agent, or Firm* — Fish & Richardson P.C.

(57) ABSTRACT

An automatic external defibrillator including: a sensor for detecting when a rescuer is delivering a CPR chest compression to the patient; electrodes for application to the thorax of the patient for delivering a defibrillation shock to the patient and for detecting an ECG signal; defibrillation circuitry for delivering a defibrillation shock to the electrodes; and a processor and associated memory for executing software that controls operation of the defibrillator. The software provides: ECG analysis for analyzing the ECG signal to determine if the cardiac rhythm is shockable; CPR detection for analyzing the output of the sensor to determine when a CPR chest compression has been delivered, and integration of the ECG analysis and CPR detection so that the determination of whether the cardiac rhythm is shockable is based only on time periods of the ECG signal during which there has not been a CPR chest compression delivered.

3 Claims, 3 Drawing Sheets

U.S. PATENT DOCUMENTS

| | | | |
|---|---|---|---|
| 4,619,265 A * | 10/1986 | Morgan et al. | 607/6 |
| 4,680,708 A | 7/1987 | Ambos et al. | |
| 4,757,821 A | 7/1988 | Snyder | |
| 4,781,200 A | 11/1988 | Baker | |
| 4,928,674 A * | 5/1990 | Halperin et al. | 601/44 |
| 5,077,667 A * | 12/1991 | Brown et al. | 607/5 |
| 5,081,993 A | 1/1992 | Kitney et al. | |
| 5,092,341 A | 3/1992 | Kelen | |
| 5,109,862 A | 5/1992 | Kelen et al. | |
| 5,193,537 A | 3/1993 | Freeman | |
| 5,247,945 A | 9/1993 | Heinze et al. | |
| 5,285,792 A | 2/1994 | Sjoquist et al. | |
| 5,330,526 A | 7/1994 | Fincke et al. | |
| 5,348,008 A | 9/1994 | Bornn et al. | |
| RE34,800 E | 11/1994 | Hutchins | |
| 5,391,187 A | 2/1995 | Freeman | |
| 5,409,010 A | 4/1995 | Beach et al. | |
| 5,439,483 A | 8/1995 | Duong-Van | |
| 5,466,244 A | 11/1995 | Morgan | |
| 5,471,991 A | 12/1995 | Shinnar | |
| 5,472,453 A | 12/1995 | Alt | |
| 5,474,574 A * | 12/1995 | Payne et al. | 607/7 |
| 5,496,257 A * | 3/1996 | Kelly | 601/41 |
| 5,507,778 A | 4/1996 | Freeman | |
| 5,511,553 A | 4/1996 | Segalowitz | |
| 5,562,710 A | 10/1996 | Olsen et al. | |
| 5,589,639 A | 12/1996 | Antonio et al. | |
| 5,591,213 A | 1/1997 | Morgan | |
| 5,611,815 A * | 3/1997 | Cole et al. | 607/5 |
| 5,617,853 A | 4/1997 | Morgan | |
| 5,619,265 A | 4/1997 | Suzuki et al. | |
| 5,645,571 A | 7/1997 | Olson et al. | |
| 5,662,690 A | 9/1997 | Cole et al. | |
| 5,674,253 A * | 10/1997 | Adams et al. | 607/7 |
| 5,683,424 A | 11/1997 | Brown et al. | |
| 5,700,281 A | 12/1997 | Brewer et al. | |
| 5,735,879 A * | 4/1998 | Gliner et al. | 607/7 |
| 5,755,671 A | 5/1998 | Albrecht et al. | |
| 5,772,604 A | 6/1998 | Langberg et al. | |
| 5,792,190 A | 8/1998 | Olson et al. | |
| 5,957,856 A | 9/1999 | Weil et al. | |
| 5,967,995 A | 10/1999 | Shusterman et al. | |
| 6,021,349 A | 2/2000 | Arand et al. | |
| 6,125,298 A * | 9/2000 | Olson et al. | 607/5 |
| 6,125,299 A | 9/2000 | Groenke et al. | |
| 6,155,257 A | 12/2000 | Lurie et al. | |
| 6,171,257 B1 * | 1/2001 | Weil et al. | 600/518 |
| 6,174,295 B1 * | 1/2001 | Cantrell et al. | 601/41 |
| 6,178,357 B1 | 1/2001 | Gliner et al. | |
| 6,188,928 B1 | 2/2001 | Noren et al. | |
| 6,224,562 B1 | 5/2001 | Lurie et al. | |
| 6,246,907 B1 | 6/2001 | Lin et al. | |
| 6,263,238 B1 * | 7/2001 | Brewer et al. | 607/5 |
| 6,306,107 B1 | 10/2001 | Myklebust et al. | |
| 6,308,094 B1 | 10/2001 | Shusterman et al. | |
| 6,334,070 B1 | 12/2001 | Nova et al. | |
| 6,351,671 B1 * | 2/2002 | Myklebust et al. | 607/5 |
| 6,360,125 B1 | 3/2002 | Weil et al. | |
| 6,390,996 B1 | 5/2002 | Halperin et al. | |
| 6,393,316 B1 | 5/2002 | Gillberg et al. | |
| 6,418,342 B1 | 7/2002 | Owen et al. | |
| 6,427,685 B1 | 8/2002 | Ray, II | |
| 6,438,419 B1 | 8/2002 | Callaway et al. | |
| 6,496,731 B1 * | 12/2002 | Lovett | 607/14 |
| 6,572,547 B2 | 6/2003 | Miller et al. | |
| 6,575,914 B2 | 6/2003 | Rock et al. | |
| 6,597,943 B2 | 7/2003 | Taha et al. | |
| 6,658,290 B1 | 12/2003 | Lin et al. | |
| 6,671,545 B2 | 12/2003 | Fincke | |
| 6,687,540 B2 | 2/2004 | Marcovecchio | |
| 6,697,671 B1 * | 2/2004 | Nova et al. | 607/5 |
| 6,827,695 B2 * | 12/2004 | Palazzolo et al. | 601/41 |
| 6,961,612 B2 * | 11/2005 | Elghazzawi et al. | 607/6 |
| 6,990,373 B2 * | 1/2006 | Jayne et al. | 607/5 |
| 6,993,386 B2 * | 1/2006 | Lin et al. | 607/5 |
| 7,006,865 B1 * | 2/2006 | Cohen et al. | 607/5 |
| 7,013,176 B2 | 3/2006 | Ding et al. | |
| 7,032,596 B2 * | 4/2006 | Thompson et al. | 128/205.13 |
| 7,085,601 B1 * | 8/2006 | Bardy et al. | 607/5 |
| 7,089,055 B2 * | 8/2006 | Cates et al. | 607/4 |
| 7,220,235 B2 * | 5/2007 | Geheb et al. | 601/41 |
| 2001/0047140 A1 * | 11/2001 | Freeman | 601/41 |
| 2002/0026131 A1 | 2/2002 | Halperin | |
| 2002/0055694 A1 | 5/2002 | Halperin et al. | |
| 2002/0133197 A1 | 9/2002 | Snyder et al. | |
| 2002/0165471 A1 | 11/2002 | Halperin et al. | |
| 2002/0165585 A1 | 11/2002 | Dupelle et al. | |
| 2002/0193711 A1 | 12/2002 | Halperin et al. | |
| 2003/0023277 A1 * | 1/2003 | Owen et al. | 607/5 |
| 2003/0055460 A1 | 3/2003 | Owen et al. | |
| 2003/0083586 A1 | 5/2003 | Ferek-Petric | |
| 2003/0083699 A1 | 5/2003 | Hamilton et al. | |
| 2003/0088285 A1 * | 5/2003 | Marcovecchio et al. | 607/5 |
| 2003/0130697 A1 * | 7/2003 | Halperin et al. | 607/2 |
| 2003/0144699 A1 * | 7/2003 | Freeman | 607/5 |
| 2003/0195567 A1 * | 10/2003 | Jayne et al. | 607/5 |
| 2004/0044374 A1 | 3/2004 | Weinberg et al. | |
| 2004/0049234 A1 * | 3/2004 | Morgan et al. | 607/5 |
| 2004/0058305 A1 | 3/2004 | Lurie et al. | |
| 2004/0059237 A1 | 3/2004 | Narayan et al. | |
| 2004/0162585 A1 | 8/2004 | Elghazzawi et al. | |
| 2004/0171954 A1 | 9/2004 | Holman | |
| 2004/0210171 A1 | 10/2004 | Palazzolo et al. | |
| 2004/0210172 A1 * | 10/2004 | Palazzolo et al. | 601/41 |
| 2004/0215244 A1 * | 10/2004 | Marcovecchio et al. | 607/5 |
| 2004/0267324 A1 * | 12/2004 | Geheb et al. | 607/5 |
| 2005/0021094 A1 * | 1/2005 | Ostroff et al. | 607/5 |
| 2005/0027317 A1 * | 2/2005 | Langer | 607/5 |
| 2005/0070964 A1 * | 3/2005 | Hansen et al. | 607/5 |
| 2005/0119706 A1 | 6/2005 | Ideker et al. | |
| 2005/0256415 A1 | 11/2005 | Tan et al. | |
| 2005/0267325 A1 | 12/2005 | Bouchier et al. | |
| 2006/0116724 A1 | 6/2006 | Snyder | |
| 2006/0122648 A1 * | 6/2006 | Elghazzawi et al. | 607/5 |
| 2006/0129190 A1 * | 6/2006 | Sullivan et al. | 607/5 |
| 2006/0129191 A1 * | 6/2006 | Sullivan et al. | 607/5 |
| 2006/0136000 A1 * | 6/2006 | Bowers | 607/5 |
| 2006/0155336 A1 * | 7/2006 | Heath | 607/5 |
| 2006/0173498 A1 * | 8/2006 | Banville et al. | 607/5 |
| 2006/0173499 A1 * | 8/2006 | Hampton et al. | 607/5 |
| 2006/0173500 A1 * | 8/2006 | Walker et al. | 607/5 |
| 2006/0173501 A1 * | 8/2006 | Stickney et al. | 607/5 |
| 2006/0206152 A1 * | 9/2006 | Covey et al. | 607/5 |
| 2006/0229679 A1 * | 10/2006 | Joo | 607/5 |
| 2006/0259080 A1 * | 11/2006 | Vaisnys et al. | 607/5 |
| 2007/0179539 A1 * | 8/2007 | Degroot et al. | 607/5 |
| 2007/0219588 A1 * | 9/2007 | Freeman | 607/5 |
| 2007/0233197 A1 * | 10/2007 | Jung et al. | 607/5 |
| 2008/0009908 A1 * | 1/2008 | Parascandola et al. | 607/5 |
| 2008/0015645 A1 * | 1/2008 | Kelly et al. | 607/5 |
| 2008/0033494 A1 * | 2/2008 | Swerdlow | 607/5 |
| 2008/0033495 A1 * | 2/2008 | Kumar | 607/5 |
| 2008/0046015 A1 * | 2/2008 | Freeman et al. | 607/6 |

FOREIGN PATENT DOCUMENTS

| | | |
|---|---|---|
| EP | 1079310 | 2/2001 |
| GB | 9713345.8 | 6/1997 |
| WO | 98/30282 | 7/1998 |
| WO | 99/24114 | 5/1999 |
| WO | 99/25306 | 5/1999 |
| WO | 01/56652 | 8/2001 |
| WO | 01/66182 | 9/2001 |
| WO | 02/15836 | 2/2002 |
| WO | 03/009895 | 2/2003 |
| WO | 2004/054656 | 7/2004 |
| WO | 2005/021089 | 3/2005 |

OTHER PUBLICATIONS

Afonso et al., "Detecting Ventricular Fibrillation", IEEE Engineering In Medicine and Biology, vol. 14:2, pp. 152-159 (1995).

Al-Fahoum et al., "Combined wavelet transformation and radial basis neural networks for classifying life-threatening cardiac arrhythmias", Medical & Biological Engineering & Computing, vol. 37:5, pp. 566-573 (1999).

Amann et al., Reliability of Fibrillation Detection Algorithms In Automatic External Defibrillators (AEDs), Dept. of Anaesthesia and Intensive Care Medicine, Leopold-Franzens-Universitat Innsbruck, Anichstr. 35, A-6020 Innsbruck, Austria, Dept. of Computer Science, Applied Mathematics Group, FH-Vorarlberg, Achstr. 1, A-6850 Dornbirn, Austria. At the top of the paper I have is the following: Jahrestaguug der Osterreichischen Deutschen und Schweizerischen Gesellschaft fur Biomedizimische Technik Sep. 2003.

Barro et al., "Algorithmic sequential decision-making in the frequency domain for life threatening ventricular arrhythmias and imitative artifacts: a diagnostic system", J. Biomed. Eng., vol. 11:4, pp. 320-328 (1989).

Botsivaly et al., "Evaluation of a new technique for the Detection of Ventricular Fibrillation and Ventricular Tachycardia", Procs of the $22_{nd}$ Ann EMBS Int Conf, Chicago, IL (2000).

Callaway et al., "Scaling exponent predicts defibrillation success for out-of-hospital ventricular fibrillation cardiac arrest," Circulation 103(12):1656-1661 (2001).

Callaway et al., "Ventricular Fibrillation Waveform Predicts Defibrillation Success by Automatic External Defibrillators", Academic Emergency Medicine, vol. 7:5, pp. 1-2 (2000).

Cardiac Science Brochure, Analysis Algorithm Overview, Powerheart® AED Automated External Defibrillator with RHYTHMx® Technology, (1999).

Clayton et al., "Comparison of four techniques for recognition of ventricular fibrillation from the surface ECG", Medical & Biological Engineering & Computing, vol. 31:2, pp. 111-117 (1993).

Eftestol et al., "Effects of Interrupting Precordial Compressions on the Calculated Probability of Defibrillation Success During Out-of-Hospital Cardiac Arrest," Circulation, 105, 2270-2273, (2002).

Eftestøl et al., "Predicting Outcome of Defibrillation by Spectral Characterization and Nonparametric Classification of Ventricular Fibrillation in Patients With Out-of-Hospital Cardiac Arrest", Circulation, 102:1523-1529 (2000).

Efestol et al., "Probability of successful defibrillation as a monitor during CPR in out-of-hospital cardiac arrested patients," Resuscitation 48(3):245-254 (2001).

Fitzgibbon et al., "Determination of the noise source in the electrocardiogram during cardiopulmonary resuscitation", Crit Care Med, vol. 30:4, pp. S148-S152 (2002).

Ge et al., "Cardiac arrhythmia classification using autoregressive modeling", Biomed Eng. Online, pp. 13, (2002).

Geheb, Frederick J., "A System for the Determination of Ventricular Tachycardia or Ventricular Fibrillation during Cardio-Pulmonary Resuscitation", 2 pages (Apr. 2002).

Haykin, Adaptive Filter Theory, Third Edition, Upper Saddle River, NJ, USA. Prentice-Hall, 1996.

Husoy et al., "Removal of Cardiopulmonary Resuscitation Artifacts From Human ECG Using an Efficient Matching Pursuit-Like Algorithm", IEEE Transactions on Biomedical Engineering, vol. 49:11, pp. 1287-1298 (2002).

Khadra et al., "Detection of life-threatening cardiac arrhythmias using the wavelet transformation", Medical & Biological Engineering & Computing, vol. 35:5, pp. 626-632 (1997).

Kuo et al., "Computer Detection of Ventricular Fibrillation", Computers in Cardiology, pp. 347-349 (Sep. 1978).

Langhelle et al. "Reducing CPR Artifacts in Ventricular Fibrillation in Vitro," Resuscitation. Mar; 48(3):279-91 (2001).

Lightfoot et al., "Dynamic nature of electrocardiographic waveform predicts rescue shock outcome in porcine ventricular fibrillation," Ann. Emerg. Med. 42(2):230-41 (Aug. 2003).

Menegazzi et al., "Immediate defibrillation versus interventions first in a swine model of prolonged ventricular fibrillation", Resuscitation, vol. 59, pp. 261-270 (2003).

Menegazzi et al., "Ventricular Fibrillation Scaling Exponent Can Guide Timing of Defibrillation and Other Therapies", Circulation, 109:926-931 (Feb. 2004).

Nygards et al., "Recognition of Ventricular Fibrillation Utilizing The Power Spectrum of The ECG", Computers in Cardiology, pp. 393-397 (1997).

Povoas et al., "Predicting the success of defibrillation by electrocardiographic analysis," Resuscitation 53(1):77-82 (2002).

Sato et al., "Adverse effects of interrupting precordial compression during cardiopulmonary resuscitation," Critical Care Medicine, vol. 25(5), 733-736 (1997).

Sherman et al., "Ventricular fibrillation exhibits dynamical properties and self-similarity", Resuscitation, vol. 47, pp. 163-173 (2000).

Wang et al., "Effects of Biphasic vs Monophasic Defibrillation on the Scaling Exponent in a Swine Model of Prolonged Ventricular Fibrillation", Academic Emergency Medicine, vol. 8:8, pp. 771-780 (2001).

Watson et al., "A novel wavelet transform based analysis reveals hidden structure in ventricular fibrillation", Resuscitation, vol. 43:2, pp. 121-127 (2000).

Yu et al., "Adverse Outcomes of Interrupted Precordial Compression During Automated Defibrillation", Circulation, pp. 368-372 (Jul. 2002), (2003).

U.S. Appl. No. 10/421,652 (Marcovecchio, Optical Pulse Sensor for External Defibrillator), (Apr. 2003).

Aase et al., "Compression Depth Estimation for CPR Quality Assessment Using DSP on Accelerometer Signals," IEEE Transactions on Biomedical Engineering, vol. 49, No. 3, Mar. 2002.

American Red Cross—Adult CPR/AED Training—Workplace Programs, http://www.redcross.org/hss/cpraed.html, printed from Internet May 14, 1999.

Force Sensing Resistors—An Overview of the Technology, FSR Integration Guide & Evaluation Parts Catalog with Suggested Electrical Interfaces, Jun. 2000.

Gruben et al., "System for Mechanical Measurements During Cardiopulmonary Resuscitation in Humans," IEEE Transactions on Biomedical Engineering, vol. 37, No. 2, Feb. 1990.

Heartstream—The Background Behind Our Technology, http://www.heartstream.com/techbk.htm, printed from Internet Jun. 25, 1999.

Flewelling, Nellcor Incorporated, Noninvasive Optical Monitoring, Chap. 88, pp. 1346-1353. CRC Press, Inc., 1995.

* cited by examiner

FIG. 6

CPR SENSITIVE ECG ANALYSIS IN AN AUTOMATIC EXTERNAL DEFIBRILLATOR

CROSS-REFERENCE TO RELATED APPLICATION

This application is a continuation application of and claims priority to application Ser. No. 10/370,036 filed Feb. 19, 2003, now U.S. Pat. No. 6,961,612 issued on Nov. 1, 2005.

TECHNICAL FIELD

This invention relates to automatic external defibrillators (AEDs), and particularly to signal processing performed by such defibrillators.

BACKGROUND

Automated External Defibrillators include signal processing software that analyzes ECG signals acquired from the victim to determine when a cardiac arrhythmia such as Ventricular Fibrillation (VF) or shockable ventricular tachycardia (VT) exists. Usually, these algorithms are designed to perform ECG analyses at specific times during the rescue event. The first ECG analysis is usually initiated within a few seconds following attachment of the defibrillation electrodes to the patient. Subsequent ECG analyses may or may not be initiated based upon the results of the first analysis. Typically if the first analysis detects a shockable rhythm, the rescuer is advised to deliver a defibrillation shock. Following the shock delivery a second analysis is automatically initiated to determine whether the defibrillation treatment was successful or not (i.e. the shockable ECG rhythm has been converted to a normal or other non-shockable rhythm). If this second analysis detects the continuing presence of a shockable arrhythmia, the AED advises the user to deliver a second defibrillation treatment. A third ECG analysis may then be initiated to determine whether the second shock was or was not effective. If a shockable rhythm persists, the rescuer is then advised to deliver a third defibrillation treatment.

Following the third defibrillator shock or when any of the analyses described above detects a non-shockable rhythm, treatment protocols recommended by the American Heart Association and European Resuscitation Council require the rescuer to check the patient's pulse or to evaluate the patient for signs of circulation. If no pulse or signs of circulation are present, the rescuer is trained to perform CPR on the victim for a period of one or more minutes. Following this period of cardiopulmonary resuscitation (that includes rescue breathing and chest compressions) the AED reinitiates a series of up to three additional ECG analyses interspersed with appropriate defibrillation treatments as described above. The sequence of 3 ECG analyses/defibrillation shocks followed by 1-3 minutes of CPR, continues in a repetitive fashion for as long as the AED's power is turned on and the patient is connected to the AED device. Typically, the AED provides audio prompts to inform the rescuer when analyses are about to begin, what the analysis results were, and when to start and stop the delivery of CPR.

One limitation associated with many AEDs is that the period between each set of ECG analyses and shocks is pre-programmed into the device and is fixed for all rescue situations. When the application of CPR due to lack of circulation is warranted, this pre-programmed period is consumed by the delivery of rescue breaths and chest compressions. When no CPR is warranted because the last shock was effective in converting the patient to a perfusing cardiac rhythm, this pre-programmed period is consumed by periodically monitoring the patient's pulse and assuring that no relapse or re-fibrillation has occurred. Under some out-of-hospital rescue protocols, the period between successive sets of ECG analyses can be as long as 3 minutes.

It is commonly known that victims of cardiac arrest who have been successfully defibrillated sometimes relapse into ventricular fibrillation shortly after a successful shock treatment. In such cases, the rescuer who verified the presence of a pulse immediately following defibrillation and thus decided not to perform CPR, may be unaware that the victim's condition has deteriorated until the next ECG analysis is performed some 1-3 minutes later. Under these conditions, the delivery of needed defibrillation treatments and CPR may be delayed.

Some AEDs are designed to avoid this undesirable delay in treatment by continuously and automatically analyzing the victim's ECG whenever defibrillation electrodes are connected to the patient. These AEDs perform a continuous "background" analysis that evaluates the victim's ECG signals during the 1-3 minute CPR/monitoring period between analysis/shock sequences. As such, they are able to detect refibrillation of the victim's heart (should it occur) and promptly advise the rescuer of the patient's deteriorated condition. While these "improved" systems help prevent the delay in treatment that can result from undetected refibrillation of the patient's heart, they are also susceptible to misinterpreting the ECG artifact introduced by CPR related chest compressions as shockable arrhythmias. When the ECG analysis algorithm misinterprets CPR related ECG artifact as a shockable rhythm, it may advise the rescuer to prematurely stop performing CPR and to deliver a defibrillation treatment. While in some cases immediate defibrillation may be the appropriate treatment, some clinical research suggests that an appropriately long period of CPR between sequences of defibrillation treatments may be more beneficial to the patient than immediate defibrillation, particularly when VF has been of long duration or persistently recurring. Furthermore when the victim's cardiac rhythm is not treatable by defibrillation therapy (non-shockable) but incompatible with life such as in cases of asystole or electromechanical disassociation, the premature cessation of CPR in response to the erroneous detection of a shockable cardiac rhythm can reduce the patient's chances of survival.

For those AEDs that perform background ECG analysis during periods between analysis/shock sequences, a common strategy for ensuring that sufficient time is provided for effective CPR delivery even in the presence of shockable rhythms is to disable background ECG analysis or ignore the results of this analysis for a predetermined time period following the last shock in each treatment sequence. During this period, the rescuer is allowed to perform CPR without advice from the unit that a shockable rhythm is present. Following this period, ECG analysis results are used to prompt the user to stop CPR and thus allow a CPR artifact free ECG analysis to be performed.

Since most currently available AEDs are not equipped to detect or monitor the delivery of CPR related chest compressions, they are incapable of determining when CPR artifact is present in the ECG signals and when it is not. The automatic activation/deactivation of their background ECG analysis function, therefore, is based exclusively upon time since the last shock or completion of the last "foreground" ECG analysis. If the delivery of CPR is stopped during this period when background ECG analyses have been disabled, life threatening changes in the patient's ECG rhythm will remain undetected (even though it could be effectively analyzed) for at least some period of time during the rescue event.

SUMMARY

In general, the invention features an automatic external defibrillator including: a sensor for detecting when a rescuer is delivering a CPR chest compression to the patient; electrodes for application to the chest of the patient for delivering a defibrillation shock to the patient and for detecting an ECG signal; and defibrillation circuitry for delivering a defibrillation shock to the electrodes. ECG analysis is performed to determine if the cardiac rhythm is shockable (i.e., treatable by defibrillation therapy). The output of the sensor is detected to determine when a CPR chest compression has been delivered. The ECG analysis and CPR detection are integrated so that the determination of whether the cardiac rhythm is treatable by defibrillation therapy is based only on time periods of the ECG signal during which there has not been a CPR chest compression delivered.

The invention improves the specificity as well as the reliability of the ECG rhythm classification. The improved reliability of ECG rhythm classification (e.g. during ECG background analysis) enhances the survival chances of victims in at least two ways. It reduces the likelihood of premature cessation of needed CPR as the result of a false detection of a shockable cardiac rhythm when the victim's cardiac rhythm is actually not treatable by defibrillation therapy (e.g., cases such as asystole or electromechanical disassociation, for which the more appropriate therapy is CPR). It avoids undesirable delay in treatment of re-fibrillation when it occurs, by allowing for continuously and automatically analyzing the victim's ECG during the 1-3 minute CPR monitoring periods between analysis/shock sequences.

Preferred implementations of the invention may incorporate one or more of the following:

The ECG analysis may comprise analysis of the ECG signal over a minimum ECG analysis time to determine whether the cardiac rhythm is shockable, and wherein integration of the ECG analysis and CPR detection may be done so that a determination that the cardiac rhythm is shockable is only made if the time period over which the ECG signal has been analyzed to make that determination includes a time period at least as long as the minimum ECG analysis time during which there has not been a CPR chest compression delivered.

A timer may be reset when a CPR chest compression has been delivered, and the value of the timer may be examined to determine whether the minimum ECG analysis time has been exceeded.

The ECG analysis may be reinitialized when it is determined that a CPR chest compression has been delivered, and only after the ECG analysis has been conducted for at least the minimum ECG analysis time without being reset is a determination made as to whether the cardiac rhythm is shockable.

The ECG analysis and CPR detection may be performed continuously during the period in which determinations are being made as to whether the cardiac rhythm is shockable.

Other features and advantages of the invention will be apparent from the following drawings and detailed description, and from the claims.

DETAILED DESCRIPTION

There are a great many different implementations of the invention possible, too many to possibly describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

Figure 1:
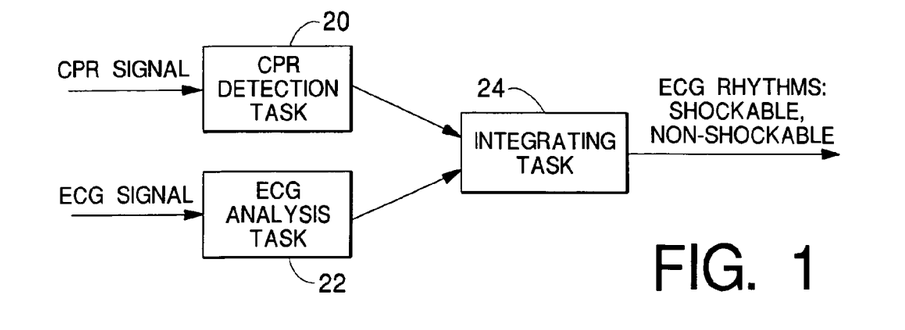
FIG. 1 is a block diagram of one implementation of the invention.

FIG. 1 shows one preferred implementation, in which the CPR detection task 20 and ECG background analysis task 22 run simultaneously and continuously during a CPR preprogrammed interval of 1 to 3 minutes. The outputs of the CPR detection task (e.g., times at which CPR compressions are delivered, amplitude of compressions, rate of compressions) and the outputs of the ECG analysis task (e.g., times at which QRS is detected, heart rate, and rhythm classification) are passed to a higher level integrating task 24. The higher level integrating task analyzes the data from both ECG and CPR tasks and qualifies ECG rhythm classifications based on the presence or absence of the detection of CPR chest compressions during the ECG analysis period. For example, if a CPR chest compression is detected, the higher level task ignores background ECG rhythm classifications for a time interval of at least X seconds after the compression, where X seconds is the minimum time interval needed by the ECG background analysis algorithm to classify an ECG rhythm. This guarantees that for the duration of at least X seconds the ECG background analysis algorithm uses a noise free ECG signal to make its classification. As a result, the number of false shockable rhythm detections due to CPR related artifact in the ECG signal is reduced and the specificity as well as the reliability of the ECG rhythm classification is improved. This improved reliability of ECG background analysis enhances the survival chances of victims in two ways: (1) it eliminates premature cessation of needed CPR as the result of a false detection of a shockable cardiac rhythm when the victim's cardiac rhythm is actually not treatable by defibrillation therapy (e.g., cases such as asystole or electromechanical disassociation, for which the more appropriate therapy is CPR); (2) it avoids undesirable delays in treatment of re-fibrillation when it occurs, by continuously and automatically analyzing the victim's ECG during the 1-3 minute CPR monitoring period between analysis/shock sequences and informing the rescuer when a shockable rhythm has been detected.

Figure 2:
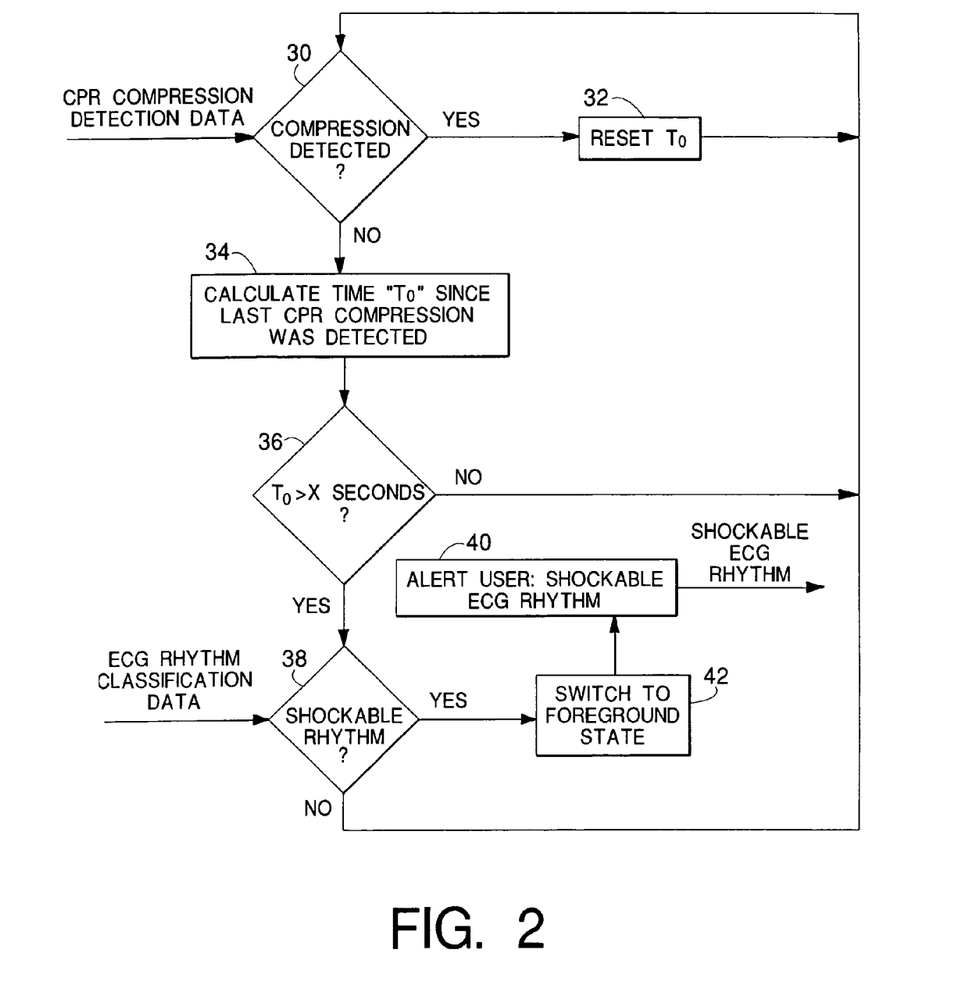
FIG. 2 is a block diagram of the integrating task of the implementation of FIG. 1.

FIG. 2 shows the process followed by the integrating task. CPR compression detection data from the CPR task and ECG rhythm classification data from the ECG task are received. The integrating task checks (30) if a compression has been detected. If a CPR compression is detected, the integrating task sets to zero (32) the elapsed time T0 since the last compression was detected and continues to execute and check for new compression detections. If no new compression is detected, the integrating task calculates (34) the elapsed time T0 since the last compression was detected. It then checks (36) to determine if T0 is greater than the time needed (X seconds) by the ECG analysis algorithm to generate a rhythm classification. If T0 is smaller than X seconds, the integrating task returns to checking for newly detected CPR compressions. Else if T0 is larger than X seconds, the integrating task moves to checking (38) the rhythm classifications being received from the ECG task. If a shockable rhythm is being reported, the integrating task alerts the user to the presence of a shockable rhythm (40) and causes the defibrillator to switch to the ECG foreground analysis state (42).

Figure 3:
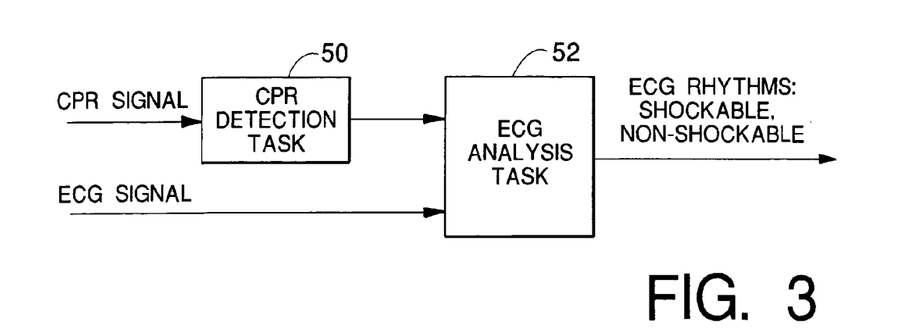
FIG. 3 is a block diagram of another implementation of the invention.

FIG. 3 shows another implementation. The CPR detection task 50 and ECG background analysis task 52 run simultaneously and continuously during a CPR preprogrammed interval. The outputs of the CPR task are passed to the ECG task, and the ECG task uses the CPR data to qualify ECG rhythm classification based on the presence or absence of the detection of CPR chest compression during the ECG analysis period. For example, if a CPR chest compression is detected, the ECG task will restart its ECG rhythm classification process, which usually requires a predefined time interval of X seconds to complete its classification of rhythms. This method guarantees that for the predefined time interval X seconds needed to classify a rhythm the ECG background analysis algorithm uses a noise free ECG signal to make its classification. As a result, the number of false shockable rhythm detections is reduced. Thus, the specificity as well as the reliability of the ECG rhythm classification is improved.

Figure 4:
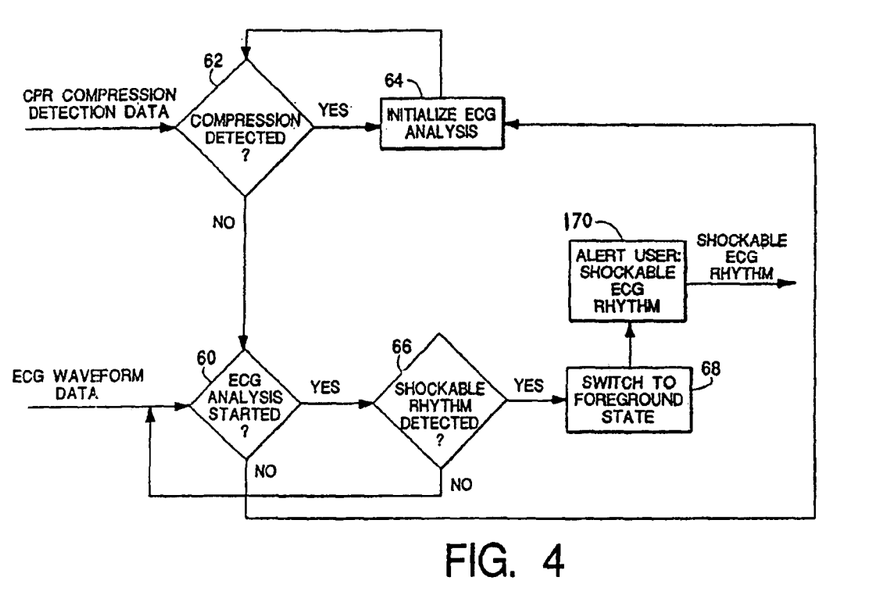
FIG. 4 is a block diagram of the ECG analysis of the implementation of FIG. 3.

FIG. 4 shows the process followed by the ECG background analysis task in the implementation of FIG. 3. The ECG task receives CPR compression detection data from the CPR task and ECG waveform data from the defibrillator front end simultaneously and continuously. Upon receiving an ECG waveform data sample, the ECG task checks (62) if a compression has been detected. If a CPR compression is detected, the ECG task reinitializes (64) the ECG analysis by restarting it from time zero. The ECG analysis task analyzes an ECG segment of data of length X seconds to determine the ECG rhythm. By initializing the ECG analysis process, the ECG task restarts its analysis of a new ECG data segment of X seconds long resulting in no ECG rhythm classification for the next X seconds. If no new compression is detected, the ECG task checks (60) if the analysis process has been initialized. If no ECG analysis is in progress, the ECG task initializes (64) the ECG analysis process. If the ECG analysis has been initialized, the ECG task continues to analyze the ECG waveform data for duration of X seconds. If no shockable rhythm is detected (66), the ECG task returns to receive the next sample. If a shockable rhythm is being reported (66), the ECG task switches to the ECG foreground analysis state (68), and alerts (170) the user to the presence of a shockable rhythm.

Figure 5:
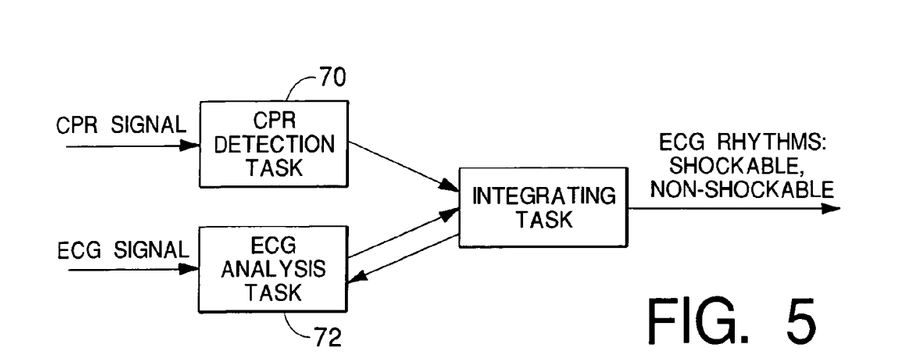
FIG. 5 is a block diagram of another implementation of the invention.

FIG. 5 shows another implementation. The CPR detection task 70 and ECG background analysis 72 task run simultaneously and continuously during a CPR preprogrammed interval of 1 to 3 minutes. The outputs of the CPR task and the outputs of the ECG task are passed to a higher level integrating task 74. This higher level integrating task analyzes the data from both ECG and CPR tasks, and reinitializes the ECG rhythm classifications when a CPR chest compression is detected. The higher level integrating task alerts the user about a shockable rhythm when reported by the ECG task. For example, if a CPR chest compression is detected, the higher level integrating task will restart the ECG rhythm classification process, which usually requires a predefined time interval of X seconds to a complete its classification of rhythms. This method guarantees that for the predefined time interval X seconds needed to classify a rhythm the ECG background analysis algorithm uses a noise free ECG signal to make its classification.

Figure 6:
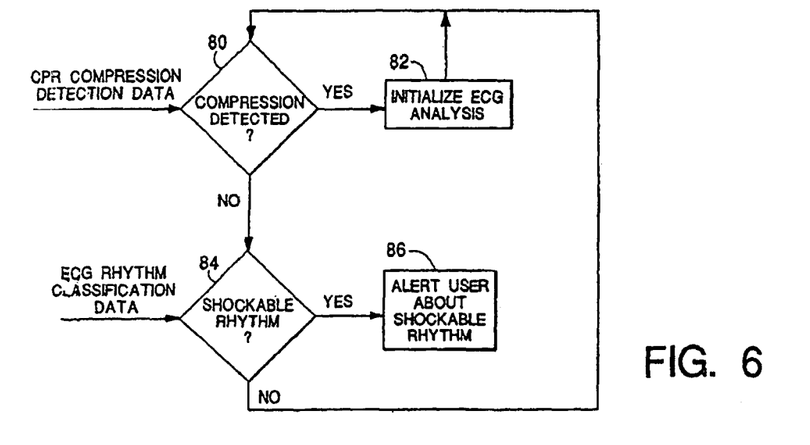
FIG. 6 is a block diagram of the integrating task of the implementation of FIG. 5.

FIG. 6 shows the process followed by the integrating task in the implementation of FIG. 5. The Integrating task receives CPR compression detection data from the CPR task and ECG rhythm classification data from the ECG task. The integrating task checks (80) if a compression has been detected. If a CPR compression is detected, the integrating task reinitializes (82) the ECG analysis by restarting it from time zero. The ECG analysis task analyzes an ECG segment of data of length X seconds to determine the ECG rhythm. By initializing the ECG analysis process, the ECG task restarts its analysis of a new ECG data segment of X seconds long resulting in no ECG rhythm classification for the next X seconds. If no new compression is detected, the integrating task checks (84) the rhythm classifications being received from the ECG task. If a shockable rhythm is being reported, the integrating task alerts the user (86) about the presence of a shockable rhythm, at which point the defibrillator switches to the ECG foreground analysis state.

Many other implementations of the invention other than those described above are within the invention, which is defined by the following claims.

What is claimed is:

1. An automatic external defibrillator for delivering defibrillation shocks to a patient, comprising
a sensor for detecting when a rescuer is delivering a CPR chest compression to the patient;
electrodes for application to the thorax of the patient for delivering a defibrillation shock to the patient and for detecting an ECG signal;
defibrillation circuitry for delivering a defibrillation shock to the electrodes;
a processor and associated memory for executing software that controls operation of the defibrillator, the software providing
ECG analysis for analyzing the ECG signal to determine if the cardiac rhythm is shockable (treatable by defibrillation therapy);
CPR detection for analyzing the output of the sensor to determine when a CPR chest compression has been delivered, and
integration of the ECG analysis and CPR detection so that the determination of whether the cardiac rhythm is shockable is based on a plurality of time periods of the ECG signal spaced apart in time during which there has not been an artifact from a delivered CPR chest compression,
wherein at least one of the time periods of the ECG signal on which the determination is based is a time period prior to delivery of a CPR chest compression and at least a second of the time periods of the ECG signal on which the determination is based is a time period after delivery of the same CPR chest compression.

2. An automatic external defibrillator for delivering defibrillation shocks to a patient, comprising
a sensor for detecting when a rescuer is delivering a CPR chest compression to the patient;
electrodes for application to the chest of the patient for delivering a defibrillation shock to the patient and for detecting an ECG signal;
defibrillation circuitry for delivering a defibrillation shock to the electrodes;
ECG analysis means for analyzing the ECG signal to determine if the cardiac rhythm is shockable (treatable by defibrillation therapy);

CPR detection means for analyzing the output of the sensor to determine when a CPR chest compression has been delivered, and integration means for integrating the ECG analysis and CPR detection so that the determination of whether the cardiac rhythm is shockable is based on a plurality of time periods of the ECG signal spaced apart in time during which there has not been an artifact from a delivered CPR chest compression, wherein at least one of the time periods of the ECG signal on which the determination is based is a time period prior to delivery of a CPR chest compression and at least a second of the time periods of the ECG signal on which the determination is based is a time period after delivery of the same CPR chest compression.

3. A method for automatically delivering defibrillation shocks to a patient, comprising applying electrodes to the chest of the patient for delivering a defibrillation shock to the patient and for detecting an ECG signal;

using a sensor to detect when a rescuer is delivering a CPR chest compression to the patient;

analyzing the ECG signal to determine if the cardiac rhythm is shockable (treatable by defibrillation therapy);

analyzing the output of the sensor to determine when a CPR chest compression has been delivered, and integrating the ECG analysis and CPR detection so that the determination of whether the cardiac rhythm is shockable is based on a plurality of time periods of the ECG signal spaced apart in time during which there has not been an artifact from a delivered CPR chest compression, wherein at least one of the time periods of the ECG signal on which the determination is based is a time period prior to delivery of a CPR chest compression and at least a second of the time periods of the ECG signal on which the determination is based is a time period after delivery of the same CPR chest compression.

* * * * *

UNITED STATES PATENT AND TRADEMARK OFFICE
CERTIFICATE OF CORRECTION

| | | |
|---|---|---|
| PATENT NO. | : 8,160,698 B2 | |
| APPLICATION NO. | : 11/264819 | |
| DATED | : April 17, 2012 | |
| INVENTOR(S) | : Ziad F. Elghazzawi et al. | |

It is certified that error appears in the above-identified patent and that said Letters Patent is hereby corrected as shown below:

Title page, (73) Assignee: "Chelsmford, MA" should be -- Chelmsford, MA --.

Signed and Sealed this
Twenty-sixth Day of June, 2012

David J. Kappos
*Director of the United States Patent and Trademark Office*